(12) United States Patent
Aviram

(10) Patent No.: US 8,927,035 B2
(45) Date of Patent: *Jan. 6, 2015

(54) METHODS AND POMEGRANATE EXTRACT COMPOSITION FOR TREATING DIABETES RELATED ATHEROSCLEROTIC COMPLICATIONS IN HUMANS

(71) Applicant: POM Wonderful, LLC, Los Angeles, CA (US)

(72) Inventor: Michael Aviram, Haifa (IL)

(73) Assignee: POM Wonderful, LLC, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/225,881

(22) Filed: Mar. 26, 2014

(65) Prior Publication Data

US 2014/0205692 A1    Jul. 24, 2014

Related U.S. Application Data

(63) Continuation of application No. 12/777,162, filed on May 10, 2010, now Pat. No. 8,734,868, which is a continuation of application No. 11/495,292, filed on Jul. 27, 2006, now Pat. No. 7,727,563, which is a continuation-in-part of application No. 11/252,842, filed on Oct. 18, 2005, now Pat. No. 7,645,469, which is a continuation of application No. 10/701,918, filed on Nov. 4, 2003, now Pat. No. 6,977,089, which is a continuation of application No. 09/998,883, filed on Nov. 19, 2001, now Pat. No. 6,641,850, which is a continuation-in-part of application No. 09/294,307, filed on Apr. 19, 1999, now Pat. No. 6,387,418.

(60) Provisional application No. 60/318,160, filed on Sep. 6, 2001.

(51) Int. Cl.
*A61K 36/185* (2006.01)

(52) U.S. Cl.
CPC .................................. *A61K 36/185* (2013.01)
USPC .......................................... 424/777; 424/725

(58) Field of Classification Search
USPC .................................... 424/725, 777
IPC ......................................... A61K 36/18,36/185
See application file for complete search history.

(56) References Cited

U.S. PATENT DOCUMENTS

| | | | | |
|---|---|---|---|---|
| 6,361,807 B1 * | 3/2002 | Aviram et al. | ................ | 424/744 |
| 6,387,418 B1 * | 5/2002 | Aviram et al. | ................ | 424/744 |
| 6,641,850 B1 * | 11/2003 | Aviram et al. | ................ | 424/769 |
| 6,977,089 B1 * | 12/2005 | Aviram et al. | ................ | 424/769 |
| 7,645,469 B2 * | 1/2010 | Aviram et al. | ................ | 424/777 |
| 7,727,563 B2 * | 6/2010 | Aviram | ................ | 424/777 |
| 7,780,998 B2 * | 8/2010 | Aviram et al. | ................ | 424/777 |

FOREIGN PATENT DOCUMENTS

JP    10298094    *    4/1992

OTHER PUBLICATIONS

Glozman et al. Khim-Farm. Zh. 1989. vol. 23, No. 9, pp. 1111-1115 (English translation).*

* cited by examiner

*Primary Examiner* — Chris R Tate
(74) *Attorney, Agent, or Firm* — Cotman IP Law Group, PLC

(57) ABSTRACT

One or more embodiments of the invention are directed to methods of using pomegranate extracts for treating diabetes related atherosclerotic complications in humans. The methods comprise the step of administering to the patients a composition comprising a therapeutically effective amount of an extract from pomegranate.

18 Claims, 5 Drawing Sheets

*p<0.01 vs. before PJ consumption

*p < 0.01 vs. controls; #p < 0.01 after PJ consumption vs. before PJ consumption.

*p < 0.01 vs. (−); #p < 0.01 vs. 0 concentration.

*p < 0.01 vs. controls HMDM.

*p < 0.01 vs. control.

METHODS AND POMEGRANATE EXTRACT COMPOSITION FOR TREATING DIABETES RELATED ATHEROSCLEROTIC COMPLICATIONS IN HUMANS

CROSS-REFERENCE TO RELATED APPLICATIONS

This application is a continuation of U.S. application Ser. No. 12/777,162, filed May 10, 2010, which is a continuation of U.S. application Ser. No. 11/495,292, filed Jul. 27, 2006, now U.S. Pat. No. 7,727,563, which is a continuation in part of U.S. Pat. No. 7,645,469, filed Oct. 18, 2005, which is a continuation of U.S. Pat. No. 6,977,089, filed Nov. 4, 2003, which is a continuation of U.S. Pat. No. 6,641,850, filed Nov. 19, 2001, which takes benefit from U.S. Provisional Patent Ser. No. 60/318,160, filed Sep. 6, 2001, and wherein U.S. Pat. No. 6,641,850 is a continuation in part of U.S. Pat. No. 6,387,418, filed Apr. 19, 1999, the specifications of which are all hereby incorporated herein by reference.

BACKGROUND OF THE INVENTION

1. Field of the Invention

One or more embodiments of the invention relate generally to a process for deriving pomegranate extracts and methods of using thereof, and more specifically but not by way of limitation to methods of using pomegranate extracts to treat diabetes related complications and atherosclerosis in humans.

2. Description of the Related Art

Diabetes mellitus is associated with increased oxidative stress and atherosclerosis development. Diabetes is increasing worldwide, resulting from the interaction of obesity, inflammation and hyperglycemia. Both type I and type II diabetes are powerful and independent risk factors for coronary artery disease, stroke and peripheral arterial disease, and atherosclerosis accounts for 80% of all deaths among diabetic patients. Prolonged exposure to hyperglycemia is now recognized as a major risk factor in the pathogenesis of atherosclerosis in diabetes. Animal and human studies elucidated three major mechanisms for the pathological alterations observed in diabetic vasculature, i.e. non-enzymatic glycosylation of proteins and lipids which can interfere with their normal function, cellular protein kinase C (PKC) activation and oxidative stress.

Diabetic patients may be highly prone to oxidative stress because hyperglycemia depletes natural anti-oxidants and facilitates the production of free radicals. Thus, anti-oxidants treatment in diabetes could be beneficial. Indeed, it was shown that alpha-tocopherol supplementation to diabetic patients significantly reduced serum oxidative stress. Furthermore, tea catechins were able to protect diabetic erythrocytes from tert-butyl hydroperoxide-induced oxidative stress.

Macrophages play a major role in the early stages of atherogenesis. Recent studies that were performed in control subjects or in diabetic patients' monocytes-macrophages demonstrated that high glucose levels can lead to macrophage foam cell formation by several mechanisms including: increased cholesterol synthesis, altered expression and secretion of lipoprotein lipase, monocytes PKC activation and up-regulation of an oxidized LDL (LOX-1) receptor, or scavenger receptors. Increased oxidative stress and increased uptake of Ox-LDL also in peritoneal macrophages from streptozotocin-induced diabetic mice, as well as in vitro, is thought to be present in cells incubated with high glucose levels.

A balanced diet, with careful attention given to the carbohydrates consumed, plays a prominent role in improving glycemia and other diabetic outcomes. As recently as 2004, the carbohydrate recommendations as stated by the American Diabetes Association (ADA) in their clinical practice recommendations for that year focused on the absolute importance of the total amount of carbohydrate consumption per meal or snack and attributed little importance to its food source. However, since evidence continues to accumulate on the efficacy of the type of carbohydrate consumed in promoting normal or improved glycemia in diabetes patients, the 2005 ADA recommendations now indicate that "use of the glycemic index/glycemic load can provide an additional benefit over that observed when total carbohydrate is considered alone". For this reason, diabetic patients usually avoid sugar-containing juices, such as grape juice, which can worsen their diabetic conditions and atherosclerotic complications.

Pomegranate juice (PJ) possesses impressive antioxidative properties due to its polyphenolics, tannins, and proanthocyanins. Consumption of PJ by humans for a period of 1 year significantly reduced the oxidation of both LDL and HDL. Furthermore, in patients with carotid artery stenosis that consumed PJ for 3 years, we demonstrated reduced oxidative stress in their blood, and a decreased atherosclerotic lesion size. PJ, which contains about 10% sugars, have similar glycemic index to that of other fruit juices such as grape juice.

A need exists, however, for a composition that has a palatable taste but still provides beneficial effects when manifested in diabetic patients with atherosclerotic complications.

BRIEF SUMMARY OF THE INVENTION

One or more embodiments of the invention are based on the unexpected discovery that pomegranate juice (which contains about 10% total sugar) consumption by a patient with diabetes does not worsen diabetic parameters and may cause anti-atherogenic effects. It was expected that pomegranate juice sugars will add to the already increased oxidative stress present in diabetic patients. This anti-atherogenicity is manifested by pomegranate juice anti-oxidant properties in serum and monocytes-macrophages, two major components of macrophage foam cell formation, the hallmark of early atherosclerosis. It is discovery of the present invention that pomegranate consumption by diabetic patients demonstrated beneficial effects by reducing cellular oxidative stress in the patient's macrophages. Accordingly, one aspect of the present invention provides a method of treating a diabetic patient to reduce atherogenicity by administration of a composition comprising an amount of an extract from pomegranate which is therapeutically effective to reduce macrophage cholesterol accumulation and foam cell formations. According to embodiments of the present invention, the atherogenicity may be increased cellular oxidative stress, macrophage foam cell formation, or increased uptake of oxidized LDL by macrophages.

At least one aspect of the present invention provides a method of treating a person with diabetes (pre-diabetes or symptoms relating thereto) having increased oxidative stress that contributes to atherosclerosis. The method comprises the step of administering to the patient a composition comprising an amount of an extract from pomegranate which is therapeutically effective to reduce the oxidative stress. This extract may take the form of a juice, a powder, oil or other polyphenol laden compositions derived from the pomegranate. Modifications to the compositions to increase the overall polyphenol count are contemplated as being within the scope and spirit of the invention. According to embodiment of the present invention, markers of the atherosclerotic and atherogenic related oxidative stress in serum may be at least one of the following: oxidized low-density lipoprotein (Ox-LDL), thiobarbituric acid reactive substances (TBARS), lipid peroxides, serum thiols (SH), gluthathione, paraoxonase 1 arylesterase (PON1), or oxidized macrophages.

One or more embodiments of the invention comprise a step of administering to a person with pre-diabetic symptoms or diabetes a composition comprising a therapeutically effective amount of an extract from pomegranate fruit. The extract of pomegranate may be a juice extract of pomegranate, an extract from inner or outer peel of pomegranate, a pomegranate derived oil or the mixture thereof.

One or more embodiments of the invention are defined in the appended claims and the full scope of any equivalents.

BRIEF DESCRIPTION OF THE DRAWINGS

The above-mentioned and other features of this invention and the manner of obtaining them will become more apparent, and will be best understood, by reference to the following description, taken in conjunction with the accompanying drawings. These drawings depict only a typical embodiment of the invention and do not therefore limit its scope. They serve to add specificity and details, in which.

DETAILED DESCRIPTION OF THE INVENTION

Figure 1:
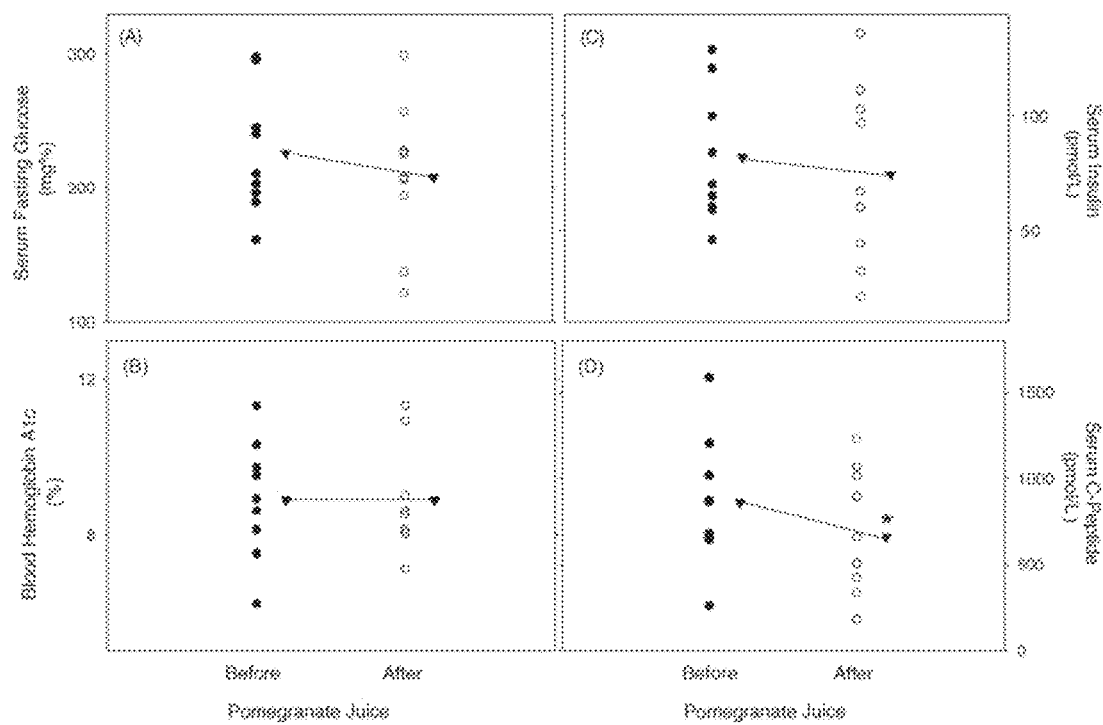
FIG. 1 shows the effect of PJ consumption by diabetic patients on diabetic parameters in serum.

One or more aspects of the present invention is directed to a method for treating a patient to slow down atherosclerosis or inhibit atherogenesis. The patient or person may have diabetes with its atherosclerotic complications. The method comprises the step of administering to a person with diabetes or pre-diabetes a composition comprising a therapeutically effective amount of an extract from pomegranate.

For the purpose of the present invention, an extract from pomegranate may be an extract from the whole pomegranate fruit or from any constituents of pomegranate fruit. Examples of constituents of pomegranate fruit that may be used to make the extract of the present invention include, but are not limited to, juice, seed, and the inner and outer peel of pomegranate fruit. In one embodiment of the present invention, the extract is the juice extract of whole pomegranate fruit. In other cases the extract is from the inner or outer peel of pomegranate fruit. In a further embodiment of the present invention, the extract may be a mixture of two or more extracts of the whole pomegranate or any constituents of pomegranate.

Methods of making the juice extract of whole pomegranate fruits are considered part of the invention. In general, any methods that may produce pomegranate juice that naturally occurs in pomegranate may be used. For the purpose of the present invention, the juice may be concentrated or diluted from its natural concentration. The juice may also be mixed with extracts of other constituents of pomegranate.

Extracts from the constituents of pomegranate, i.e., seeds or the inner or outer peel, may be made. For example, the seeds or the inner or outer peel of pomegranate may be diluted in water and the extract may be made by crushing, squeezing, or extensive vortexing. The insoluble materials of the extract may be separated from the soluble supernatant of the extract. The supernatant of the extract is used for the purpose of one or more embodiments of the invention, although any oily, lipidic fraction of the extract may also be used. The extract from constituents of pomegranate may be concentrated or diluted, or mixed with each other or with pomegranate juice extract.

In accordance with one embodiment of the present invention, the extract of the present invention may be prepared by a process including the steps of: (a) crushing and squeezing the whole fruits of the pomegranate, including the inner and outer peels and the seeds, to yield a juice component and an insoluble by-product component, and (b) separating the juice component from the insoluble by-product component. The juice component may be used as a juice extract of the present invention. The insoluble by-product component may be resuspended in an aqueous medium, such as, but not limited to, water or alcohol, and be further crushed, squeezed, and mixed to yield a soluble portion and an insoluble portion. Then the soluble portion may be separated from the insoluble portion to produce the extract of the constituents of the present invention. Alternatively, the soluble portion may be combined with the juice extract to produce the extract of the present invention.

In one embodiment of the present invention, the whole fruit of the pomegranate may be enzymatically treated to improve extraction and filtration. For example, pectinase may be used to treat the whole fruit to prevent the formation of pectin gels. Other enzymes known in the art may also be used as long as they can improve extraction and filtration of the extract of the present invention.

The extract of pomegranate of the present invention may be in a liquid or solid form. In accordance with one embodiment of the present invention, a solid form of the extract may be made by lyophilizing the liquid extract of the present invention. Alternatively, the constituents of the pomegranate, such as seeds, inner or outer peels, or any insoluble portion discussed above, may be processed directly to form the solid form of the extract of the present invention. For example, the constituents of the pomegranate may be dried, and "processed into powder or pill forms to be used directly as the solid form of the extract of the present invention. Further methods and pomegranate based compositions that may be of use in one or more embodiments of the invention are set forth in U.S. patent application Ser. No. 11/137,248 entitled "Process for Extracting Phytochemicals from Pomegranate Solids and Compositions and Methods of Use Thereof" and filed on May 24, 2005, the specification of which is hereby incorporated herein by reference.

Compositions of the present invention may be a variety of kinds, including, but not limited to, nutritional supplements, pharmaceutical preparations, vitamin supplements, food additives, or foods supplements. Compositions of the present invention may be in convenient dosage forms, including, but not limited to, tablets, suspensions, implants, solutions, emulsions, capsules, powders, syrups, liquid compositions, ointments, lotions, creams, pastes, gels, or the like.

Compositions used in one or more embodiments of the invention may include a carrier. Depending on the kind of compositions of the present invention, a carrier may be a dietary suitable carrier or a pharmaceutically acceptable carrier, as long as it is compatible with the particular kind of compositions of the present invention. Examples of a dietary suitable carrier include, but are not limited to, dietary suitable excipients, diluents, and carriers. Examples of a pharmaceutically acceptable carrier include, but are not limited to, biocompatible vehicles, adjuvants, additives, and diluents to achieve a composition usable as a dosage form. As used herein, the terms "pharmaceutically acceptable," "physiologically tolerable," and grammatical variations thereof, as they refer to compositions, carriers, diluents, and reagents, are used interchangeably and represent that the materials are capable of administration to or upon a mammal without the production of undesirable physiological effects. The composition may also include additives that increase the polyphenol content of the composition from its natural state.

The compositions of the present invention may be used alone or in combination with other biologically active ingredients. A composition of the present invention, alone or in combination with other active ingredients, may be administered to a subject in a single dose or multiple doses over a period of time, generally by oral administration. Various administration patterns will be apparent to those skilled in the art. The dosage ranges for the administration of the compositions of the present invention are those large enough to produce the desired effect. The dosage should not be so large as to cause any adverse side effects, such as unwanted cross-reactions and the like. Generally, the dosage will vary with the age, weight, sex, condition, and extent of a condition in a subject, and the intended purpose. The dosage can be determined by one of skill in the art without undue experimentation. The dosage can be adjusted in the event of any counter indications, tolerance, or similar conditions. Those of skill in the art can readily evaluate such factors and, based on this information, determine the particular effective concentration of a composition of the present invention to be used for an intended purpose.

In one embodiment of the present invention, a composition contains the extract of pomegranate in a dosage unit in an amount that contains at least 30 to 3000 μmols per dosage unit of polyphenols. For the purpose of the present invention, polyphenols are those naturally present in the extract of pomegranate. It should be appreciated that polyphenols are used herein as a measurement marker for the amount of extract that needs to be used in each dosage unit. They are not used herein as an indication that they are the active, or the only active, ingredients of the extract. In fact, it is possible that something else, or the synergy of polyphenols and other components of an extract of the present invention, may be responsible for the activities of the extract.

The term "dosage unit" as used herein refers to physically discrete units suitable as unitary dosages for subjects, each unit containing a predetermined quantity of active material calculated to produce the desired therapeutic effect in association with the required diluent, e.g., a carrier or vehicle. The specifications for the unit dose of this invention are dictated by and are directly dependent on (a) the unique characteristics of the active material and (b) the limitations inherent in the art of compounding such active material for therapeutical use in subjects.

The term "therapeutically effective amount" as used herein means that the amount of the extract of the present invention contained in the composition administered is of sufficient quantity to achieve the intended purpose, such as, in this case, to treat the patient to inhibit atherogenesis without worsening diabetic parameters. For the purpose of the present invention, treatment of atherogenicity may be measured by the change in the serum oxidative stress markers that implicates atherosclerosis. According to embodiment of the present invention, markers of the atherogenic related and atherosclerotic related oxidative stress in serum may be at least one of the following: oxidized low-density lipoprotein (Ox-LDL), thiobarbituric acid reactive substances (TBARS), lipid peroxides, serum thiols (SH), glutathione, paraoxonase 1 arylesterase (PON1), or oxidized macrophages. The measurement of the diabetic parameters may be serum levels of at least one of fasting glucose, insulin, blood hemoglobin A1c, or C-peptide. Methods of measuring the changes in the serum oxidative stress markers and measuring the diabetic parameters are well known in the art, and need not be repeated herein.

Accordingly, by determining the changes in atherosclerotic related or atherogenic related oxidative stress markers in a patient, one skilled in the art can readily determine whether the amount of the extract of the present invention is therapeutically effective in view of the disclosure of the present invention without undue experimentation. In one embodiment, the therapeutically effective amount of the extract of the present invention contains at least 30 mg/serving of polyphenols naturally occurring in a pomegranate fruit. Again, it should be appreciated that the polyphenols are used herein as a measurement marker for the concentration of the extract of the present invention. In another embodiment, the composition contains one glass of juice extract of the present invention.

The following examples are intended to illustrate, but not to limit, the scope of the invention. Indeed, those of ordinary skill in the art can readily envision and produce further embodiments, based on the teachings herein, without undue experimentation.

EXAMPLES

Methods
Subjects
Ten male healthy subjects (controls) and 10 male non-insulin dependent diabetes mellitus (NIDDM) patients (age 35-71 years old, mean age 50±10) participated in the study. The controls were non-smokers, with no diabetes (glucose levels below 100 mg % and hemoglobin A1c levels were in the range of 4.8-6.2%), hypertension or coronary artery disease, and they did not take any medications. The diabetes mellitus duration in the patients was 4-10 years, glucose levels above 160 mg %, hemoglobin A1c in the range of 7.5-11.3%. All the patients had no ischemic heart disease, no hypercholesterolemia and were no smokers, but 50% of the patients were hypertriglyceridemic with serum triglyceride levels (300-790 mg %). Eighty percent of the patients were treated with Glucophage (Metformin) and 50% with Gluben (Glybenclamid). Two of the patients were hypertensive and were treated with ACE inhibitors. The patients consumed 50 ml of pomegranate juice concentrate per day (which contain roughly 2500 mg polyphenol per liter+/−50% of total polyphenols) for a period of 3 months. (equal 8 oz. of PJ) Blood was collected from controls and from the diabetic patients before and after PJ consumption for biochemical parameters analysis. Blood was also collected from two of the controls and from three diabetic patients before and after PJ consumption for preparation of monocytes-derived macrophages.

Reagents
2',7'-Dichlorofluorescin diacetate (DCFH) was purchased from Sigma (St. Louis, Mo., USA). FITC-conjugated antibody was purchased from Serotec IQ Products (Zerinkepark, The Netherlands). PBS, DMEM, RPMI-1640 medium, FCS (heat-inactivated at 56° C. for 30 min), penicillin, streptomycin, nystatin, 1-glutamine and sodium pyruvate were purchased from Biological Industries (Beth Haemek, Israel).

Pomegranate Processing

Pomegranates were picked by hand, washed and stored in tanks The fruits were crushed and squeezed. The juice was filtered, pasteurized, concentrated and stored at −18° C. Each day along the study period, the concentrated PJ was diluted 1:5 (v/v) with water in order to obtain a single strength PJ. The anti-oxidant composition of the juice includes: roughly 1979 mg/l of tannins (1561 mg/l of punicalagin and 417 mg/l of hydrolysable tannins), 384 mg/l of anthocyanins (delphinidin 3,5-diglucoside, cyanidin 3,5-diglucoside, delphinidin-3-glucoside, cyanidin 3-glucoside and pelargonidine 3-glucoside) and 121 mg/l of ellagic acids derivatives. The juice contained also 3 mg of Vitamin C per 100 ml of PJ. For the extraction of PJ polyphenols fraction C18 sorbent column was used (Varian HF Bondesil C18 resin sorbent). Total polyphenols were eluted from the column with 1% acidified (food-grade acetic acid) ethanol.

Serum Paraoxonase 1 Activity

PON1 arylesterase activity towards phenyl acetate was determined as previously described.

Serum Lipids Peroxidation

Serum lipid peroxidation was measured before and after 3 months of PJ consumption. Serum samples were diluted ×4 with PBS, and were incubated without or with 100 mM of 2,2'-azobis, 2-amidinopropane hydrochloride (AAPH, Wako, Japan) for 2 h at 37° C. The extent of lipid peroxidation was measured by the thiobarbituric acid reactive substances (TBARS) assay and by the lipid peroxides assay.

Total Thiols (SH Groups) in Serum

The assay procedure determines the amount of protein bound SH groups, as well as glutathione. An aliquot of 50 μl serum was mixed with 1 ml of Tris-EDTA buffer, and the absorbance at 412 nm was measured. To this was added 20 μl of 10 mM DTNB, and after 15 min incubation at room temperature the absorbance was measured, together with a DTNB blank. Total SH groups are calculated as described before.

Human Monocytes-Derived Macrophages (HMDM)

HMDM were separated from the blood and plated at 106/ml in RPMI medium with 10% FCS. After 2 h of incubation at 37° C., non-adherent cells were removed, and RPMI with 10% autologous serum was added. Macrophages were analyzed 8 days after plating.

Detection of Intracellular Oxidative Stress by the DCFH Assay

Intracellular oxidative stress was assayed through the oxidation of DCFH-DA, and monitored by flow cytometry [28]. For flow-cytometric assay of DCFH-DA oxidation, cells were washed (×1) with PBS and incubated with 10 μM DCFH-DA, in medium for 30 min at 37° C. Adherent cells were detached by gentle scraping, and all cells were washed (×2) with PBS. Measurements of cellular fluorescence determined by FACS were done at 510-540 nm after excitation of the cells at 488 nm with an argon ion laser. Ten thousand events were registered for each experiment. Cellular fluorescence was quantitated by mean fluorescence intensity (MFI).

Macrophage Reduced Glutathione Content

All the preparation steps were carried out on ice. The cells from triplicate dishes (1×106 per dish) were washed, scraped from the dish and sonicated in an ultrasonic processor (3×20 s at 80 W). The amount of protein was measured by the Lowry method and reduced glutathione content by the DTNB-GSSG reductase recycling assay.

Oxidized LDL (Ox-LDL) Uptake by Macrophages

LDL was separated from plasma of normal healthy volunteers by discontinuous density-gradient ultracentrifugation and dialyzed against saline with EDTA (1 mM). LDL protein concentration was determined by the Lowry method. Before oxidation, LDL was diluted in PBS to 1 mg/ml and dialyzed overnight against PBS at 4° C. to remove the EDTA. Oxidation of LDL was carried out at 37° C. under air in a shaking water bath. LDL (1 mg/ml) was incubated for 18 h at 37° C. with freshly prepared $CuSO_4$ (5 μM, Sigma). Oxidation was terminated by refrigeration at 4° C. The extent of LDL oxidation was determined by the TBARS assay. Ox-LDL was conjugated to fluoroisothiocyanate (FITC) for cellular uptake studies. HMDM were incubated at 37° C. for 3 h with FITC-conjugated Ox-LDL at a concentration of 20 μg of protein/ml. The uptake of the lipoproteins was determined by flow cytometry. Measurements of cellular fluorescence determined by FACS were done at 510-540 nm after excitation of the cells at 488 nm with an argon ion laser. Ten thousand events were registered for each experiment. Cellular fluorescence was quantitated by mean fluorescence intensity.

Statistical Analysis

Statistical analysis was performed using the Student paired t-test when comparing the mean of two groups. ANOVA was used when more than two groups (n=10 each group) were compared and results are given as mean±S.E.M.

Results

Effect of PJ Consumption by Diabetic Patients on Serum Biochemical Parameters

The results of the serum lipid profile in healthy subjects and in diabetic patients before and after 3 month 50 ml per day pomegranate juice (PJ) consumption are summarized in Table 1. Serum total cholesterol and LDL cholesterol levels in the patients were similar to that of the controls. In contrast, serum triglyceride levels were significantly higher by 2.8-fold in the patients versus controls, whereas HDL-cholesterol levels were significantly decreased by 28%. PJ consumption by the patients did not affect these parameters.

TABLE 1

Serum lipid profile in healthy subjects (controls) and in diabetic patients before and after pomegranate juice (PJ) consumption.

| | Controls (n = 10) | Diabetic patients before PJ (n = 10) | Diabetic patients after PJ (n = 10) |
|---|---|---|---|
| Triglyceride (mg %) | 115 ± 25 | 327 ± 79* | 302 ± 64 |
| Total cholesterol (mg %) | 190 ± 9 | 203 ± 13 | 193 ± 10 |
| LDL-cholesterol (mg %) | 111 ± 10 | 112 ± 8 | 110 ± 8 |
| HDL-cholesterol (mg %) | 56 ± 3 | 39 ± 3 | 41 ± 3* |

*$p < 0.01$ vs. controls.

As PJ contains sugars we first questioned the effect of PJ consumption by the patients on serum diabetic parameters: glucose, hemoglobin (Hb) A1c, insulin and C-peptide (a cleavage product of proinsulin). Blood Hb A1c levels were significantly increased in the diabetic patients versus controls by 59% (8.9±0.5% versus 5.6±0.2%), whereas insulin and serum C-peptide levels were only slightly different in patients versus controls (82±9 pmol/l for the patient's insulin levels versus 103±8 pmol/l for the control's insulin levels, and 862±119 pmol/l for the patient's C-peptide versus 770±88 pmol/l for the control's C-peptide levels, respectively). PJ consumption by the patients resulted in a non-significant reduction, by 8%, in the serum glucose levels, with no significant effect on HbA1c levels (FIGS. 1A and 1B). Similarly, a non-significant reduction in serum insulin levels (by 9%) was noted (FIG. 1C), whereas serum C-peptide levels were significantly lower ($p<0.01$), by 23%, in patients after PJ consumption versus before (FIG. 1D). These results indicate that, in spite of the presence of sugars in consumed PJ, serum diabetic parameters were not worsen, but even improved (FIG. 1).

Effect of PJ Consumption by Diabetic Patients on Serum Oxidative Status

Diabetes is known to be accompanied by increased oxidative stress. Indeed, in our patients' serum samples we observed significant high levels of lipid peroxides and TBARS by 350% and 51%, respectively, versus the controls (FIGS. 2A and 2B). In addition serum sulfhydryl groups content (which is another marker for oxidative stress) was significantly reduced by 21% in the patients versus controls (FIG. 2C). Paraoxonase 1 is an HDL-associated lactonase/esterase which was shown to protect lipids in lipoproteins and cells from oxidation, by its ability to hydrolyze specific oxidized lipids. PON1 arylesterase activity in the patients' serum was significantly lower, by 23%, versus the controls (FIG. 2D). PJ consumption by the patients significantly reduced serum oxidative stress. The lipid peroxides and TBARS levels were decreased by 56% and 28%, respectively, as compared to the levels observed in the patients' serum before PJ consumption (FIGS. 1A and B). In parallel, serum total sulfhydryl groups content and PON1 arylesterase activity, significantly increased by 12% and 24%, respectively (FIGS. 2C and 2D).

Direct Effect of PJ on Serum Oxidative Stress: in Vitro Study

Diabetic patients' serum samples (obtained from the patients before PJ consumption) were incubated for 1 h at room temperature (25° C.) with no addition (control) or with PJ (20 μM or 40 μM of total PJ polyphenols). Then, the amount of TBARS in the basal state, as well as after AAPH-induced lipid peroxidation, was measured. PJ significantly decreased the basal amount of TBARS in the patients' serum by 17% or 24%, on using 20 μM or 40 μM of total polyphenols, respectively (FIG. 3A). Furthermore, the susceptibility of the patients' serum to AAPH-induced oxidation was also substantially decreased, by 48% and 73%, respectively (FIG. 3B). Upon adding increasing concentrations of PJ total polyphenols (0-40 μM) to diabetic patients' serum samples, PON1 arylesterase activity significantly increased in a PJ dose-dependent manner, by up to 25% (FIG. 3C).

Effect of PJ Consumption by Diabetic Patients on Cellular Oxidative Status in Their Monocytes-Derived Macrophages As diabetic patients are prone to develop accelerated atherosclerosis, and as macrophages play a major role in the early stages of atherogenesis, we next studied the oxidative status of the patients' HMDM versus controls, and the effect of PJ consumption by the diabetic patients. The level of total cellular peroxides, as measured by the DCFH assay, was significantly higher by 36% in the patients' HMDM versus controls' HMDM (FIG. 4A). PJ consumption significantly reduced the cellular lipid peroxides content by 71% (to levels which are even lower than those observed in the controls' HMDM), in comparison to the levels observed in the patients' HMDM before PJ consumption (FIG. 4A). Reduced glutathione (GSH) is a major cellular anti-oxidant against oxidative stress. In the patients' HMDM, reduced glutathione content was markedly lower, by 64%, versus the amount found in controls' HMDM, and PJ consumption by the patients resulted in elevation in the HMDM glutathione levels by 141%, almost the level observed in control HMDM (FIG. 4B). These results indicate that in diabetic patients' macrophages, and not only the serum, are under increased oxidative stress. PJ consumption by diabetic patients demonstrated beneficial effects by reducing cellular oxidative stress in the patients' macrophages. Oxidized LDL uptake by macrophages can lead to macrophage cholesterol accumulation and foam cell formation, and "oxidized macrophages" were shown to take up Ox-LDL at enhanced rate. Thus, we next compared the extent of Ox-LDL uptake by the patients' HMDM to its uptake by control HMDM. Ox-LDL uptake by the patients' HMDM was significantly increased, by 37%, as compared to controls' HMDM (FIG. 4C). PJ supplementation by the patients resulted in a substantial reduction, by 39%, in the uptake of Ox-LDL by the patients' HMDM, as compared to the values obtained before PJ consumption (FIG. 4C).

Direct Effect of PJ on Diabetic Patient HMDM Oxidative Status and on Ox-LDL Uptake: in Vitro Study Incubation of diabetic patient HMDM with PJ (75 μM polyphenols) for 20 h at 37° C. resulted in a significant reduction, by 60%, in the level of cellular peroxides, as measured by the DCFH assay (FIG. 5A). Similarly, incubation of the cells with 75 μM of the PJ-derived polyphenols fraction, significantly decreased the cellular peroxides content in the patients' HMDM by 47% (FIG. 5A). Furthermore, PJ (75 μM) incubation with diabetic HMDM, inhibited also the uptake of Ox-LDL by 30%, compared to the extent of Ox-LDL uptake by non-treated cells (FIG. 5B).

FIG. 1 shows the effect of PJ consumption by diabetic patients on diabetic parameters in serum. Ten NIDDM patients consumed PJ (50 ml per day for 3 months). Blood samples were collected from the patients before PJ consumption and after 3 months of PJ consumption. Serum fasting glucose (FIG. 1A), hemoglobin A1c (FIG. 1B), insulin (FIG. 1C) and C-peptide (FIG. 1D) levels were determined.

Figure 2:
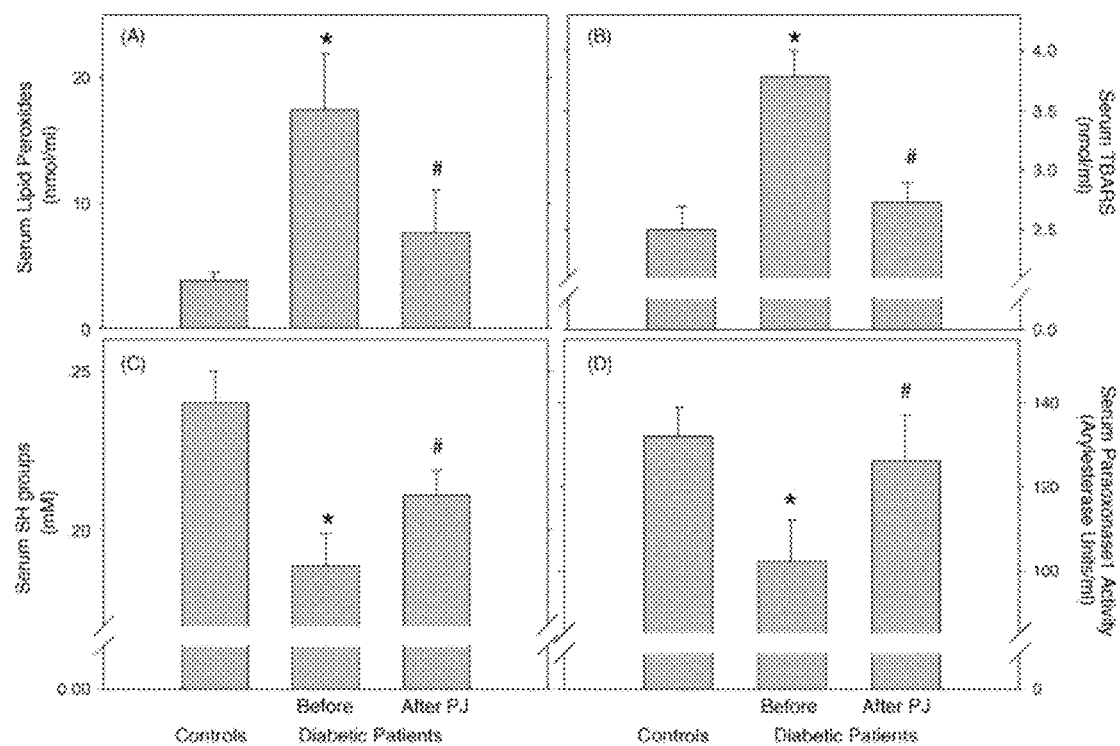
FIG. 2 shows the effect of PJ consumption by diabetic patients on serum oxidative status.

FIG. 2 shows the effect of PJ consumption by diabetic patients on serum oxidative status. Ten NIDDM patients were compared to 10 healthy subjects (controls). The patients consumed PJ (50 ml per day for 3 months). Blood samples were collected from the controls and from the patients before and after PJ consumption. The oxidative status of the serum samples was determined by the lipid peroxides (FIG. 2A) and TBARS (FIG. 2B) assays. Total serum thiols (SH) groups levels (FIG. 2C) and paraoxonase 1 arylesterase activity (FIG. 2D) were measured as described under Methods section.

Figure 3:
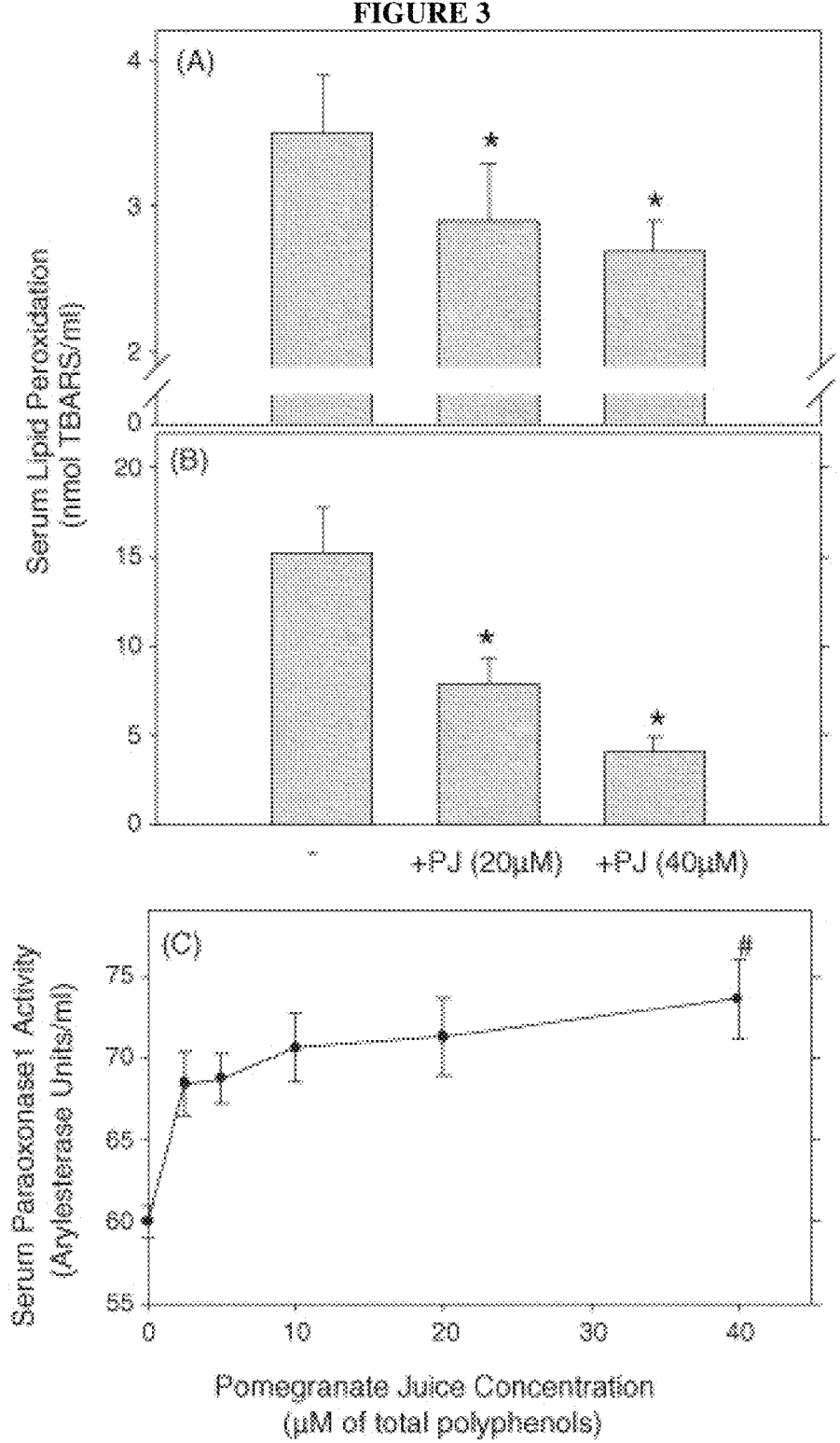
FIG. 3 shows the effect of PJ on serum oxidative status and on paraoxonase activity: in vitro study.

FIG. 3 shows the effect of PJ on serum oxidative status and on paraoxonase activity: in vitro study. Serum from diabetic patients (n=3) was incubated for 1 h without (−) or with PJ 20 μM or 40 μM polyphenols. Then, the serum was diluted ×4 with PBS and (FIG. 3A) incubated for 2 h at 37° C. with no addition (basal) or (FIG. 3B) with 100 mM of the free radical generator AAPH (AAPH-induced). At the end of the incubation period, the amount of TBARS in all the samples was determined. FIG. 3C shows the serum from the diabetic patients was incubated with increasing (0-40 μM) PJ polyphenols concentrations for 1 h at room temperature. Then, paraoxonase 1 arylesterase activity was measured as described under Methods section.

Figure 4:
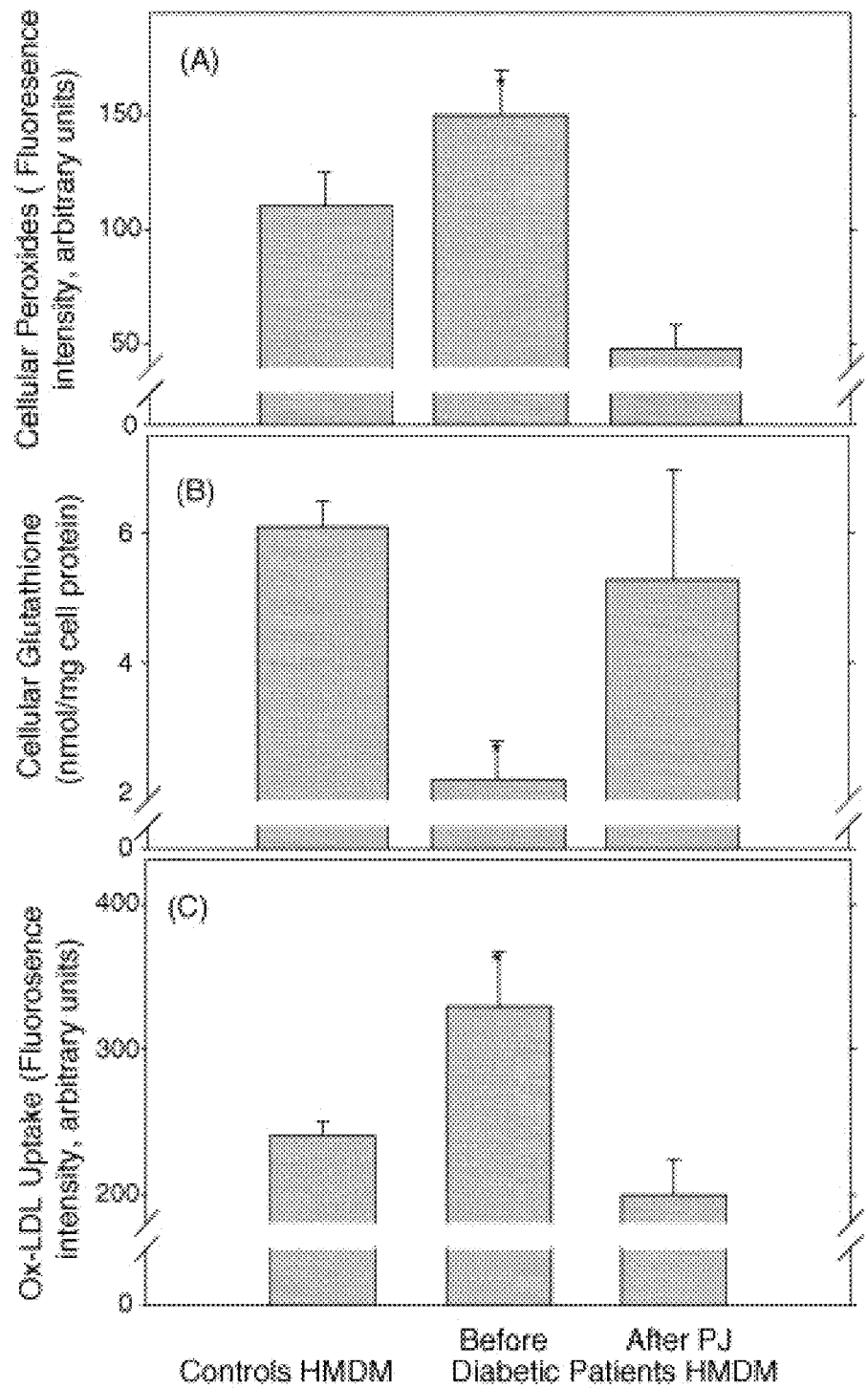
FIG. 4 shows the effect of PJ consumption by diabetic patients on human monocytes-derived macrophages (HMDM) oxidative status.

FIG. 4 shows the effect of PJ consumption by diabetic patients on human monocytes-derived macrophages (HMDM) oxidative status. Monocytes were isolated from the blood of two healthy subjects (controls) and from three NIDDM patients before and after 3 months of PJ consumption (50 ml per day), as described under Method Section. The monocytes were differentiated into macrophages in the presence of RPMI medium containing 10% autologous serum. After 7 days in culture the amount of cellular peroxides (FIG. 4A) of reduced glutathione (FIG. 4B) and the uptake of Ox-LDL (20 μg of protein/ml) labeled with FITC by the cells (FIG. 4C) were determined as described under Methods section.

Figure 5:
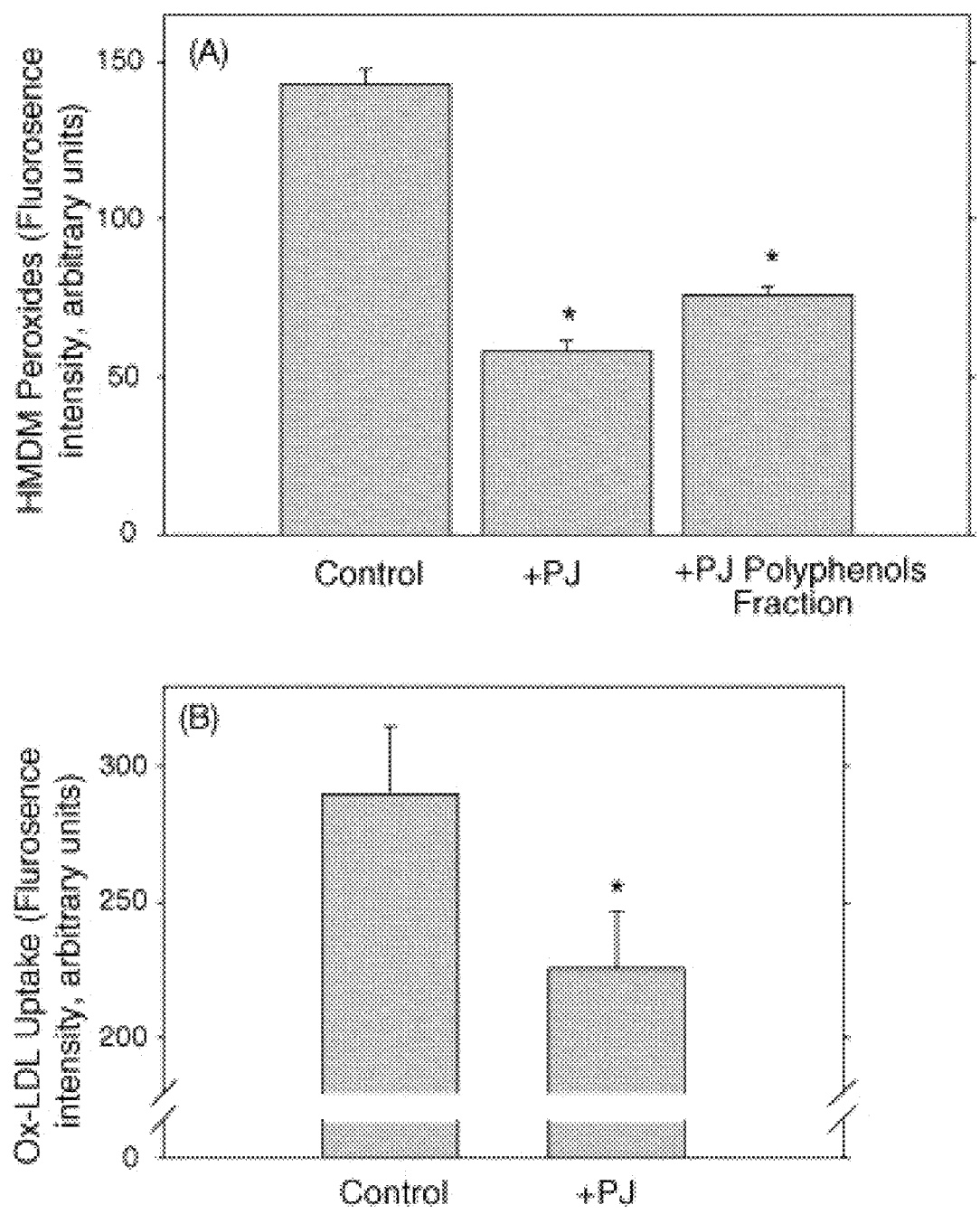
FIG. 5 shows the effect of PJ on diabetic patients' monocytes-derived macrophages (HMDM) oxidative status, and on the ability of the cells to take up Ox-LDL: in vitro study.

FIG. 5 shows the effect of PJ on diabetic patients' monocytes-derived macrophages (HMDM) oxidative status, and on the ability of the cells to take up Ox-LDL: in vitro study. Monocytes were isolated from the blood of three NIDDM patients before PJ consumption. After their differentiation into macrophages in the presence of RPMI medium+10% autologous serum, at day 6, the cells were incubated with no addition (control), with PJ 75 µM polyphenols concentration (+PJ), or with 75 µM of PJ polyphenols fraction. FIG. 5A shows the level of cellular peroxides was determined by the DCFH assay. FIG. 5B shows the uptake of Ox-LDL (20 µg of protein/ml) labeled with FITC was analyzed as described under Methods section.

Discussion

The present study demonstrated that pomegranate juice consumption by diabetic patients (as previously shown for healthy subjects and atherosclerotic patients) did not worsen the diabetic parameters, but rather resulted in anti-atherogenic effects with a significant reduction in oxidative stress in the patients' serum and monocytes-macrophages, as well as in macrophage uptake of Ox-LDL.

Diabetic patients versus control healthy subjects have significant high serum triglyceride levels and low HDL-cholesterol levels, as previously shown. Diabetic patients usually avoid sugar-containing juices which worsen their diabetic markers and atherosclerotic complications. In the present study, we showed that PJ (which contain 10% total sugars) consumption by the diabetic patients did neither increase serum glucose, nor blood HbA1c levels even though PJ glycemic index is similar to that of other fruit juices.

In the patients' serum versus controls we observed increased oxidative stress (high levels of lipid peroxides and aldehydes, and low levels of SH groups), as was previously shown for diabetes. The increased serum oxidative stress in the patients could be the result of glycation and glycooxidation of LDL by glucose, or/and the decreased capability of the patients' HDL to protect LDL against oxidation. HDL-associated paraoxonase protects LDL and HDL against oxidation, by its ability to hydrolyze specific oxidized lipids. Serum paraoxonase 1 (PON1) activity in our patients versus controls was significantly lower as was previously shown, and this fact may account for the increased serum oxidative stress. Indeed, it was demonstrated that Ox-LDL levels and vascular complications in type II patients are in correlation with PON1 activity. The reduced PON1 activity in the patients could resulted from PON1 inactivation by oxidized lipids, or by glucose. As oxidative stress may have a role in the onset and progression of diabetes and its complications, anti-oxidants were suggested as a possible treatment. Anti-oxidants such as Vitamin E and red wine were shown to reduce oxidative stress in the patients' serum. In accordance with these studies, the present study clearly demonstrated that PJ consumption by diabetic patients significantly reduced serum oxidative stress as shown previously in healthy subjects and in patients with carotid artery stenosis. This effect of PJ may be related to its potent tannins and anthocyanins which scavenge wide spectrum of free radicals, as well as to PJ-induced increment in the diabetic patients serum PON1 activity as previously shown. The increased PON1 activity could have resulted from the reduction in oxidative stress (less PON1 inactivation), and/or from the direct effect of the pomegranate juice component(s) on the enzyme activity as shown in vitro (FIG. 3).

Increased oxidative stress was shown not only in the patients' serum, but also in the patients' monocytes-macrophages (increased cellular levels of peroxides and decreased levels of macrophage reduced glutathione). Similar results were noted in peritoneal macrophages from streptozotocin-induced diabetic mice, and also in vitro in macrophages that were incubated with high glucose levels. The increased oxidative stress in the patients' HMDM could be related to cellular mechanisms induced by the high glucose levels such as, PKC activation followed by the production of free radicals. In the present study, PJ consumption significantly reduced cellular peroxides in the patients' HMDM, as was previously shown in carotid lesions from carotid artery stenosis (CAS) patients that consumed PJ. This effect could be due to the increased serum PON1 activity, which can hydrolyze lipid peroxides on the macrophage surface, or to a direct effect of pomegranate juice component(s). Indeed, in vitro we observed that both PJ and the PJ-derived polyphenolic fraction, significantly reduced macrophage oxidative stress. The PJ polyphenolic fraction was less potent than PJ, indicating that other factors in the juice (unique sugars) contribute to cellular oxidative stress reduction. We have recently shown indeed that PJ reduced oxidative stress in J774A.1 macrophage cell line, and this effect was PJ polyphenols dose-dependent.

As glucose increases oxidative stress, it was expected that PJ sugars will add to the already increased oxidative stress present in diabetic patients. Surprisingly it did not, and in fact PJ significantly decreased oxidative stress in serum, as well as in their monocytes-macrophages.

The uptake of Ox-LDL by the patients' HMDM was significantly increased as compared to control HMDM. This phenomenon could be related to the increased expression of the scavenger receptor CD36, which is induced by glucose and/or by the high oxidative stress. Similar results were observed in diabetic, streptozotocin-injected mice. PJ consumption by the patients, as well as a direct in vitro incubation of PJ with the patients' HMDM resulted in a significant reduction in Ox-LDL uptake by the patients' HMDM. Similar results were noted upon incubating J774A.1 macrophages with PJ. PJ-induced reduction in the cellular uptake of Ox-LDL could not be related to down-regulation of the scavenger receptor CD36 mRNA expression. However, CD36 is not the only surface binding for Ox-LDL by macrophages. PJ component(s) also interact with other scavengers receptors such as the SR-A or LOX-1 (which are also up-regulated by glucose), or with proteoglycans which were shown to mediate uptake of Ox-LDL by macrophages. PJ polyphenols could possibly also interfere with the uptake of Ox-LDL by interaction with macrophage surface phospholipids and/or kinases.

It is an unexpected discovery of the present invention that pomegranate juice consumption by diabetic patients does not worsen diabetic parameters, but rather act as an anti-atherogenic agent. This anti-atherogenicity is manifested by PJ anti-oxidant properties in serum and monocytes-macrophages, two major components of macrophage foam cell formation, the hallmark of early atherosclerosis.

The present invention may be embodied in other specific forms without departing from its essential characteristics. The described embodiment is to be considered in all respects only as illustrative and not as restrictive. The scope of invention is, therefore, indicated by the appended claims rather than by the foregoing description. All changes which come within the meaning and range of the equivalence of the claims are to be embraced within their scope.

What is claimed is:

1. A composition for treating diabetes-related symptoms comprising:
    a therapeutically effective amount of a pomegranate composition, wherein said therapeutically effective amount of said pomegranate composition comprises an amount sufficient to result in anti-atherogenic effects with a significant reduction in oxidative stress in said patient's serum and monocytes-macrophages, as well as in macrophage uptake of Ox-LDL to a patient to affect at least one diabetes-related symptom, wherein said pomegranate composition comprises about 1979 mg/L of tannins and is obtained from a process comprising:

crushing, squeezing, and enzymatically treating whole fruits of pomegranate including inner and outer peels and seeds to yield a juice component and an insoluble by-product component;

separating the juice component from the insoluble by-product component;

resuspending the insoluble by-product component in an aqueous medium;

crushing, squeezing, and mixing the resuspended by-product component to yield a soluble portion and an insoluble portion;

separating the soluble portion from the insoluble portion; and combining the soluble portion with the juice component to produce the pomegranate composition.

2. The composition of claim 1, wherein said at least one diabetes-related symptom comprises a pre-diabetic symptom.

3. The composition of claim 1, wherein said therapeutically effective amount is administered daily.

4. The composition of claim 1, wherein said pomegranate composition comprises about 2500 mg/L polyphenols from pomegranate.

5. The composition of claim 1, wherein said pomegranate composition comprises a punicalagin content equivalent to about 1561 mg/L.

6. The composition of claim 1, wherein said pomegranate composition comprises concentrated pomegranate juice diluted 1:5 (v/v) with water.

7. The composition of claim 1, wherein said pomegranate composition comprises a pomegranate polyphenol fraction.

8. The composition of claim 1, wherein said pomegranate composition comprises a pharmaceutically acceptable carrier.

9. The composition of claim 1, wherein said therapeutically effective amount of said pomegranate composition affects said at least one diabetes-related symptom by reducing oxidative stress in a patient.

10. The composition of claim 9, wherein said therapeutically effective amount of said pomegranate composition reduces AAPH-induced oxidation in said patient.

11. The composition of claim 9, wherein said therapeutically effective amount of said pomegranate composition reduces serum lipid peroxide level in said patient.

12. The composition of claim 9, wherein said therapeutically effective amount of said pomegranate composition reduces thiobarbituric acid reactive substances level in said patient.

13. The composition of claim 9, wherein said therapeutically effective amount of said pomegranate composition increases serum thiols groups level in said patient.

14. The composition of claim 9, wherein said therapeutically effective amount of said pomegranate composition inhibits uptake of oxidized low-density lipoprotein in said patient.

15. The composition of claim 9, wherein said therapeutically effective amount of said pomegranate composition increases serum total sulfhydryl groups content of said patient.

16. The composition of claim 1, wherein said therapeutically effective amount of said pomegranate composition reduces macrophage cholesterol accumulation in a patient.

17. The composition of claim 1, wherein said therapeutically effective amount of said pomegranate composition reduces macrophage foam cell formation in a patient.

18. A composition for treating diabetes-related symptoms of a diabetic patient comprising:

a therapeutically effective amount of a pomegranate composition to reduce oxidative stress in a diabetic patient, wherein said pomegranate composition comprises about 1979 mg/L of tannins, and wherein said therapeutically effective amount of said pomegranate composition comprises a quantity sufficient to result in anti-atherogenic effects with a significant reduction in oxidative stress in said patient's serum and monocytes-macrophages, as well as in macrophage uptake of Ox-LDL, wherein said pomegranate composition is obtained from a process comprising:

crushing, squeezing, and enzymatically treating whole fruits of pomegranate including inner and outer peels and seeds to yield a juice component and an insoluble by-product component;

separating the juice component from the insoluble by-product component;

resuspending the insoluble by-product component in an aqueous medium;

crushing, squeezing, and mixing the resuspended by-product component to yield a soluble portion and an insoluble portion;

separating the soluble portion from the insoluble portion; and combining the soluble portion with the juice component to produce the pomegranate composition, wherein said pomegranate composition is diluted 1:5 (v/v) with water.

* * * * *